United States Patent [19]
Buckman

[11] 3,982,534
[45] Sept. 28, 1976

[54] INTRAVENOUS ADMINISTRATION SYSTEM

[76] Inventor: Thomas P. Buckman, 11561 Shelly Vista Drive, Tujunga, Calif. 91042

[22] Filed: Jan. 10, 1975

[21] Appl. No.: 539,953

[52] U.S. Cl. .......................... 128/214 C; 128/214.2; 128/227; 222/145
[51] Int. Cl.² .......................................... A61M 5/16
[58] Field of Search ........ 128/214 R, 214 C, 214 D, 128/214.2, 227; 222/145

[56] References Cited
UNITED STATES PATENTS

| | | | |
|---|---|---|---|
| 2,999,499 | 9/1961 | Willet.............................. | 128/214 R |
| 3,216,419 | 11/1965 | Scislowicz....................... | 128/214 C |
| 3,217,711 | 11/1965 | Pecina et al. .................... | 128/214 C |
| 3,521,635 | 7/1970 | Koehn............................. | 128/214 C |
| 3,756,237 | 9/1973 | Chittenden et al. ........... | 128/214 R X |
| 3,776,229 | 12/1973 | McPhee .......................... | 128/214 C |
| 3,785,378 | 1/1974 | Stewart........................... | 128/214 C |
| 3,886,937 | 6/1975 | Bobo et al....................... | 128/214 R |

FOREIGN PATENTS OR APPLICATIONS

| | | | |
|---|---|---|---|
| 737,249 | 6/1966 | Canada........................... | 128/214 R |

*Primary Examiner*—Dalton L. Truluck
*Attorney, Agent, or Firm*—Witherspoon and Lane

[57] ABSTRACT

An intravenous administration system comprising three separate units adapted for cooperative use for specified intravenous medication. The apparatus comprises a primary I.V. set, a secondary or series I.V. set and a volumetric I.V. set. All sets are made up of modules some of which are common to each set thereby affording substantial savings in stocking of components. The primary I.V. set provides the standard basic I.V. fluid while the volumetric set may be used with the primary to provide introduction of a second medicament through the add-medication site of the primary set. Flow of the medicament from the volumetric set may be volumetrically and periodically controlled. If an added medicament of either compatible or non compatible nature is required, such may be administered by means of the secondary I.V. set which is connected to the primary set. The purpose of the secondary I.V. set is to provide economy in administration of fluids as the secondary I.V. is "piggybacked" into the primary set, and therefore no flow control valve is required for the secondary set.

23 Claims, 10 Drawing Figures

U.S. Patent  Sept. 28, 1976  Sheet 2 of 4  3,982,534
FIG. 2.
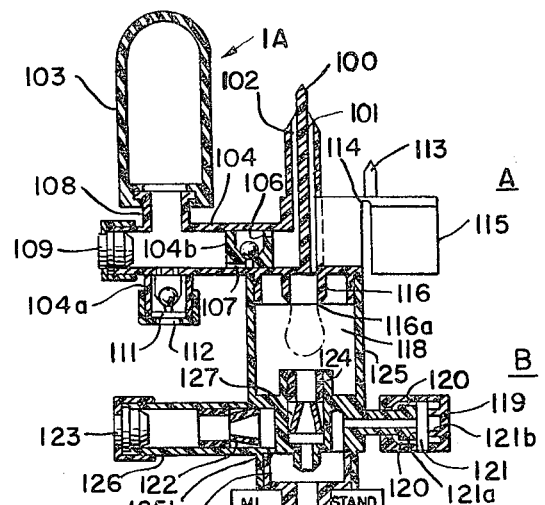
FIG. 3A.
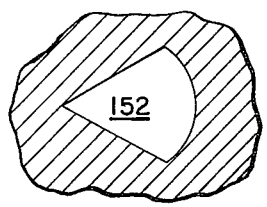
FIG. 3B.
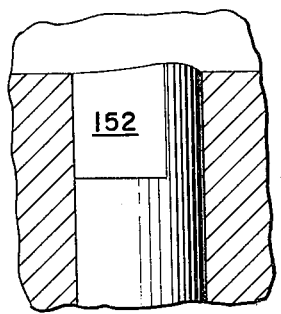
FIG. 8.
FIG. 3C.
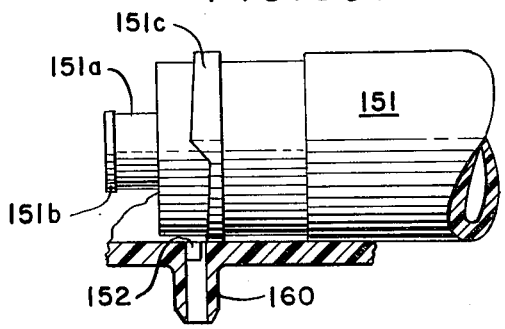
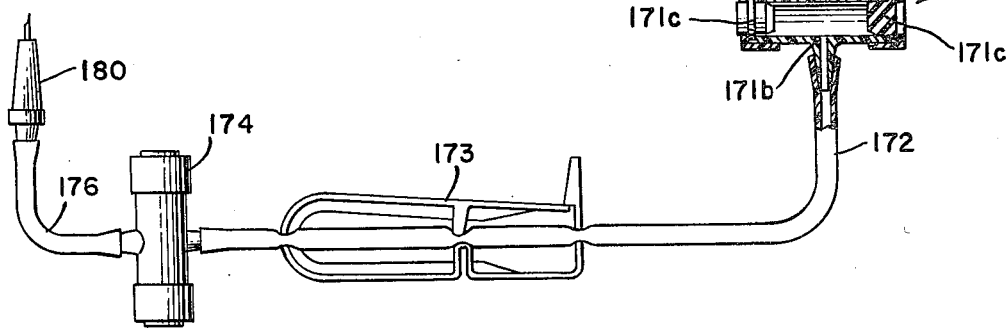

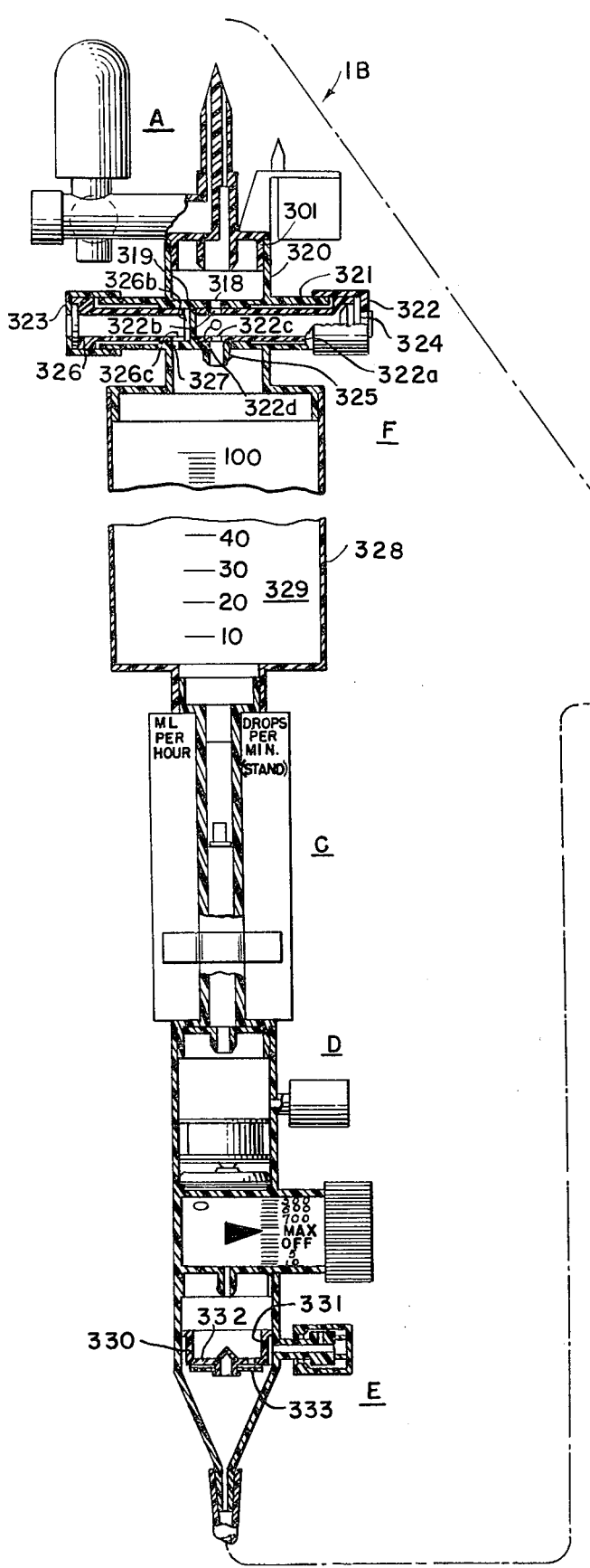
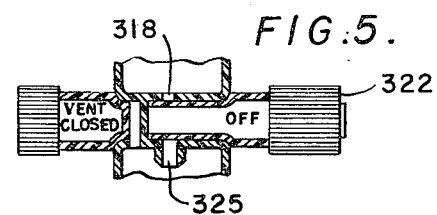
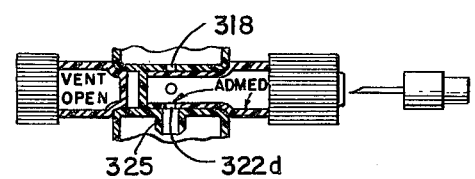
FIG. 5.
FIG. 6.
FIG. 4.

3,982,534

INTRAVENOUS ADMINISTRATION SYSTEM

SUMMARY OF THE INVENTION

This invention is directed to apparatus for administering intravenous solutions and more particularly relates to such apparatus which comprises a primary set, a volumetric set and a secondary set all of which may be connected to provide a multitude of necessary intravenous administrations.

Modern technology has developed many medicaments and other related parenteral solutions which are best introduced into the patient by intravenous means. Due to the nature of the solutions involved, very accurate administering must be provided. Further, the intravenous apparatus must be susceptible of a wide range of uses with regard to time and flow quantity and must also need little or no readjustment once the apparatus is set up. Also, the apparatus must prevent air emboli from entering a patient's vein.

In view of the foregoing, it is an object of this invention to provide an intravenous administering system which comprises accurately controlled flow from several sources through a single cannula inserted in the patient.

It is another object of the invention to provide an intravenous administering system wherein flow from one source will be automatically started when another source is exhausted.

It is a further object of this invention to provide an intravenous administering system having means to prevent air lock when the apparatus is inverted in the attaching of a new I.V. container.

It is yet another object of the invention to provide intravenous apparatus which is readily adaptable for many different types of intravenous administration.

The above and additional objects and advantages will become more apparent when taken in conjunction with the following detailed description and drawings.

In the drawing:

FIG. 2 is a front elevational view, partly in section, illustrating the primary parenteral unit.

FIG. 3a is a plan view of FIG. 3b showing the valve opening in the flow control valve assembly.

FIG. 3b is an enlarged cross section view of the valve seat in the flow control assembly.

FIG. 3c is an enlarged view of the flow control valving means in combination with the valve seat showing the helical method of controlling flow rate.

FIG. 4 is a front elevational view, partly in section, showing the volumetric parenteral unit.

FIG. 5 is a sectional view of the three-way valve embodied and module F and illustrates the closed position of the valve.

FIG. 6 is a view similar to FIG. 5 and shows the valve in open position to receive and feed I.V. fluid from an external source.

FIG. 8 is a sectional view taken along line 8—8 of FIG. 2 illustrating the means for removing air bubbles from the bottom surface of the flow motor float.

DETAILED DESCRIPTION OF THE INVENTION

Figure 1:
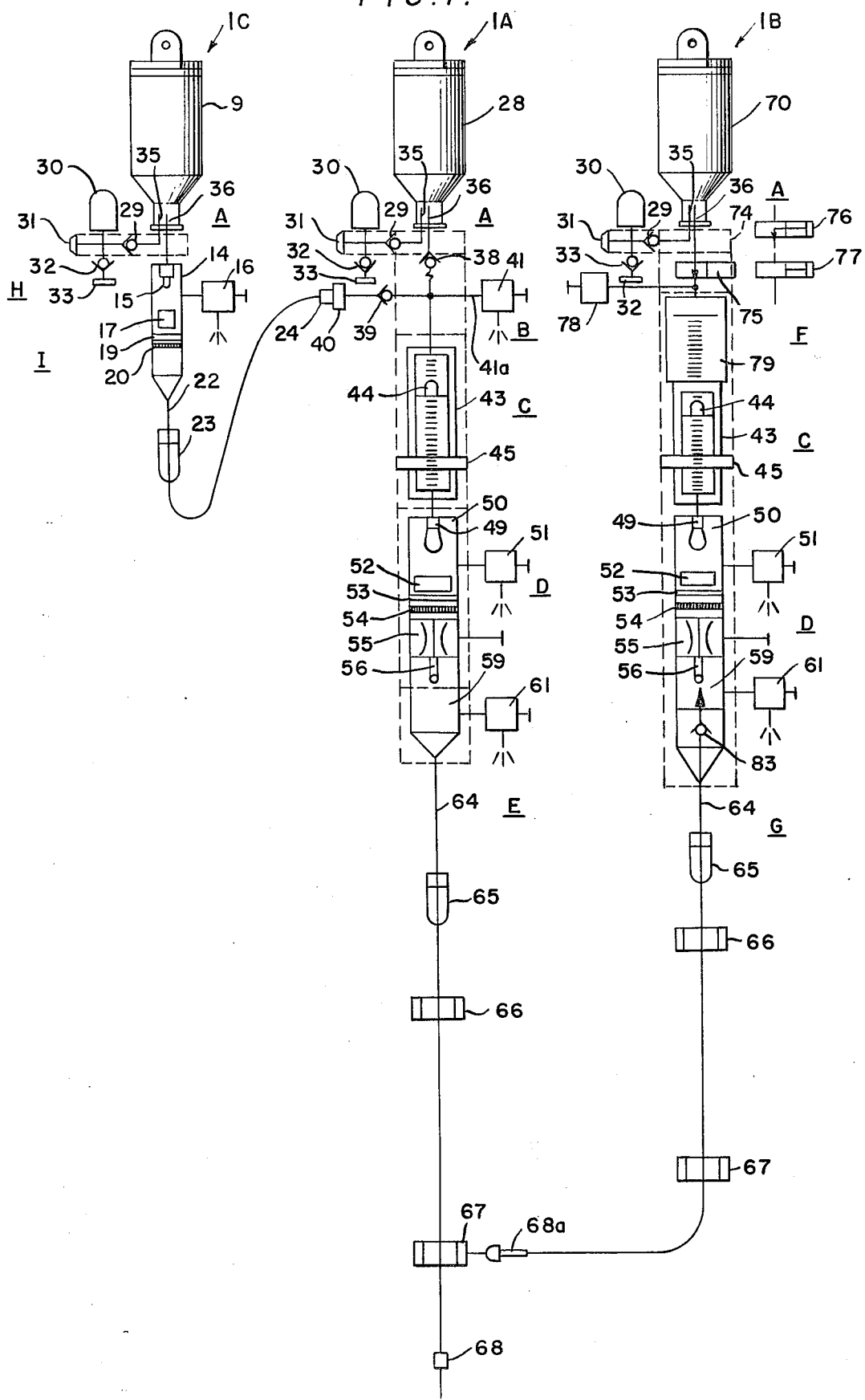
FIG. 1 is a schematic drawing showing the general arrangement of the entire apparatus of this invention which comprises a primary I.V. set, a secondary I.V. set and a volumetric I.V. set arranged for independent or combined operation.

Referring to Schematic FIG. 1, the entire I.V. apparatus of this invention comprises a primary I.V. unit 1A, a secondary or piggyback I.V. unit 1C and a volumetric I.V. set 1B. More particularly, the primary I.V. unit 1A comprises five modules as follows:
1. the spike and pump module A including a pump 30, filtered air inlet 33 and check valve 32, infusion site 31, pump outlet check valve 29, air passage 35 and fluid passage 36;
2. a vent assembly module B including primary check valve 38, secondary check valve 39, infusion site 40 and vent valve 41;
3. flow meter module C including flow meter 43, float 44 rate band 45;
4. flow control module D having a standard sized drop tube 49, anti-airlock valve chamber 50, vent valve 51, anti-air lock and anti-air embolism valve 52, filter retainer 53, filter 54, flow control valve 55 and micro-drop tube 56; and
5. fluid reservoir and administration module E including a micro drop chamber reservoir 59, vent valve 61, tubing 64, clamp 65, infusion sites 66 and 67 and cannula assembly 68.

The volumetric set 1B comprises five modules as follows:
1. a spike and pump assembly A exactly like that found in the primary set 1A
2. a valve, vent valve and burette module F comprising housing 74, three-way valve 75 connected to the I.V. container 70 to control flow from the I.V. container 70; to control flow from a piggyback unit or to cut off all fluid flow, vent valve 78 and burette 79. The three-way valve 75 as it would appear when connected for flow from a piggyback unit is illustrated at 76 while shut off is depicted at 77;
3. flow meter module C is identical with flow meter module C in primary set 1A;
4. flow control module D is identical with the flow control module D of the primary set 1A; and
5. fluid reservoir and administration module G comprising a micro drop chamber reservoir 59, vent valve 61, attenuator assembly 83, tubing 64, clamp 65, infusion sites 66 and 67 and cannula assembly 68a.

The secondary set 1C comprises three modules
1. a spike and pump module A which is identical to the spike and pump module A of the primary set 1A;
2. an anti-air lock and anti-air embolism module H comprising a housing 14, a micro drop chamber 15, anti-air lock float valve 17, valve seat and filter retainer 19, filter 20, vent valve 16, and
3. administration module I including tubing 22, clamp 23 and cannula assembly 24.

IN OPERATION

1. Consider that the primary set 1A is being used alone. The secondary and volumetric sets may be interconnected to the primary set, but their clamps would be in the closed position.

With the intravenous fluid container 28 filled with 50 ml, 250 ml, 1000 ml or whatever volume is required and suspended from an IV hook, no fluid flows through the set apparatus until pump 30 is actuated, "no flow" being caused by back pressure of check valve 38 and the minuteness of the micron sized pores in filter 54.

When pump 30 is depressed a few times rapidly in succession, air is drawn in through the air inlet filter 33, pushed through check valve 32 and then air passage 35 up into the container 28 whereupon fluid is forced down passage 36 and on through the apparatus.

During set up for the establishment of a prescribed flow rate, air is displaced by fluid in the flow meter 43, the anit-air lock valve chamber 50, and the reservoir chamber 59. To displace air in flow meter chamber 43, vent valve 41 is retained open until fluid level parallels the vent tube 41a, which is the tube connecting chamber 43 with the vent valve 41. For each of the other two chambers 50 and 59, vent valves 51 and 61 are retained open until fluid level parallels their respective vent tubes. To prevent anit-air lock valve 52 from being retained on its seat, clamp 65 is depressed to the off position before proceeding to vent the system. Then as chamber 50 is filled, the anti-air lock valve 52 will proceed to float off its seat. Then by opening vent valve 61 the anti-air embolism chamber 59 can be filled.

The next step is to purge the administration tubing system. Clamp 65 is opened. Flow control valve 55 is turned to the max open position. When all air emboli are drained out cannula 68, the control valve is adjusted until the flow meter float 44 stabilizes at the prescribed flow rate which can be from 2 ml per hour to approximately 600 ml per hour.

2. Consider that the secondary piggyback set is being utilized in conjunction with the primary. The secondary set 1C may be attached to any size container from 50 ml to 1000 ml. If the primary 1A is to be used for keep open service at 10 to 20 ml per hour, the primary is prepared as in step 1 above, and flow control valve 55 is adjusted to the required keep open flow rate. The secondary set 1C is then purged of all air emboli as in the primary set 1A and promptly connected to said primary set via cannula 24 into infusion site 40. Flow rate from the secondary container 9 will then proceed at the rate set for the primary. Check valve 39 has less back pressure than check valve 38 of the primary, and therefore the secondary will continue to flow until the supply in the container is exhausted or clamp 23 is manually closed.

When the secondary container 9 is exhausted, fluid level in the anti-air lock chamber 15 drops until the anti-air lock valve 17 shuts off the flow by seating on the filter retainer seat 19, thereby preventing any air emboli from clogging micronic filter 20 or from flowing down the tubing and causing a stoppage of flow of the primary system.

With the secondary 1C automatically shut off the primary system 1A takes over and flow rate from the primary I.V. container continues at the previous setting. The primary system will continue to flow until either the container 28 is exhausted or shut off clamp 65 is closed.

If the doctor specifies alternate flow between the secondary and the primary, such as 100 ml of the secondary medication followed by 100 ml of the primary, the nurse would adjust the flow rate of the primary until the float 44 in the flow meter 43 stabilizes at 100 ml per hour. She would then open clamp 23 on the secondary and leave it open until 1 hour passed whereupon she would close the clamp 23. If the primary should then flow at a different flow rate, she would make the adjustment on the flow control valve 55 and permit flow to continue for a given period of time whereupon she would again open the clamp 23 on the secondary.

3. Consider that the volumetric set 1B is being utilized in conjunction with the primary 1A. In the above instance of alternating flow between the primary set 1A and a secondary set 1C it would be more advantageous to incorporate the volumetric set for the secondary set as the burette could be filled with 150 ml or less of solution and a precise volume metered into the patient. When the volume is delivered, the primary set, if the needle of the volumetric unit is inserted into the piggyback infusion site 40 of the primary 1A would continue to flow at keep open or whatever flow rate is prescribed. On the other hand, if the needle of the volumetric set 1B is inserted into lower infusion site 67 of the primary, both the primary and the volumetric set might flow at the same time, which is dangerous where incompatible fluids are used. If the administration tubing infusion site is used for infusion from the volumetric set and incompatible fluids are involved, clamp 65 of the primary system is closed when the volumetric set is flowing, and clamp 65 of the volumetric set is closed when the primary set is flowing.

The primary I.V. set 1A is shown in detail in FIG. 2 and comprises a spike 100 having an air inlet 102 in fluid connection with tubular housing 104 which contains check valves 104a and 104b as well as an infusion site 109 in its end portion. An air pump 103 is attached to a necked section 108 extending upwardly from the housing 104. Check valve 104a is provided with a filter 111 to filter air drawn into the housing 104 by means of pump 103. Check valve 104b is provided with a side inlet 107 and a side outlet 106 to feed air to the spike air inlet 102. Housing 104 is also provided with an integral plug 113 having an attached finger grip number 115. A weakened section 114 is formed between the housing 104 and the plug 113 whereby the plug may be broken off and used to break the seal 112 on check valve 104a to allow air to be drawn therethrough by the pump 103. Spike 100 is provided with a fluid passage 101 which feeds fluid down into drop forming tube 116 extending downwardly from the housing 104. At its open end the drop forming tube 116 has a chambered end terminating in a sharp edge 116a to help in preventing fluid flow up the outside of the tube 116.

The vent valve assembly, module B, comprises a tube 125 forming a micro drop chamber 118 and connected to housing 104 so as to surround tube 116. The lower end of the tube 125 is provided with a horizontally extending feed tube 126 housing a check valve 122 that acts to control flow of fluid introduced through diaphragm seal 123 positioned at the outer end of said tube. The lower end of tube 125 has a cylindrical outlet 124 which is smaller than the diameter of said tube. The aforesaid outlet 124 housing a check valve 127 which prevents upward flow of fluid. The operational pressures of check valves 122 and 127 are such that free flow through feed tube 126 will occur prior to flow through outlet 124. Vent valve 119 is mounted on the lower end of tube 125 and comprises valve passages 120 cut off by valve disc 121 biased against valve seat 121a by spring means 121b.

Flow meter assembly, module C, includes a downwardly extending enlarged cylindrical section 125c connected to and fitting within connecting collar 125b projecting downwardly from the lower end of tube 125. The cylindrical section 125C is fluidly in communication with feed tube 126, outlet 124 and vent valve 119. A flow meter tube 129 extends downwardly from cylindrical section 125C and has a tapered bore 129b which is largest at the bottom and smallest at the top. A shoulder 129c is formed around the bore 129b near the top thereof to act as an upper stop for float 130 which rides up and down in said bore. The float 130 is provided with a bulbous float cap 131 and a base 132 which is adapted to engage the aforesaid shoulder 129c. The base 132 is outwardly flared to act as an indicator to cooperate with adjacent milliliter per hour and drops per minute scales 134 and 135 respectively to indicate fluid flow. A slide band indicator 136 is mounted on flow meter tube 129. A standard drop tube 137 extends downwardly from the lower extremity of the flow meter tube 129.

As illustrated in FIG. 8, means are provided for removing air bubbles from the bottom surface of the float base 132. This means comprises a central restricting hole 137b of approximately 0.040 diameter extending through the float horizontal position 137c of the drop tube 137. A pluarlity of radially disposed grooves 137d are connected to the hole 137b whereby when the bottom surface of the float base 132 rests on the flat horizontal portion 137c of the drop tube 137 the restricting hole 137b and connected radial grooves 137d will be the only source of flow and hence will produce increased flow velocity to maintain desired flow quantity. The velocity is sufficient to wash out any air emboli which may be adhering to the bottom surface of the float base 132.

The flow control assembly, module D, comprises a flow tube 139 connected to downwardly projecting flow meter collar 138 said flow tube 139 forming a drop chamber 140 into which drop tube 137 feeds. A float valve assembly 144 is positioned in the lower portion of drop chamber 140 and has a conical valve 144a which cooperates with a conformingly shaped opening in the valve seat and filter retainer 146 to control flow therethrough. Filter discs 147 are placed immediately beneath the filter retainer 146 and rest on the bottom 148 of the flow tube 139. Intermediate the extremities of the flow tube 139 there is located a vent valve 142. The bottom 148 is formed with an opening 148a through which fluid is fed to the flow control valve assembly 149.

The flow control valve assembly 149 comprises a horizontal cylindrical housing 150 rotatably carrying within it a cylindrical valve 151. The valve 151 has a stem 151a of reduced diameter which rides in annular flange bearing 150a extending inwardly from housing 150. The housing is provided with a pie shaped outlet 152 running axially thereof. (See FIG. 3A) Pie shaped outlet opening 152 is progressively and adjustably opened and closed by a peripheral and graduated valve closure surface 151c on the valve 151. A micro drop tube 160 is in communication with and extends downwardly from the opening 152 to receive the controlled fluid flow. The valve 151 is provided with a peripheral dial scale 157 adapted to cooperate with index mark 158 on the housing 150 to indicate flow rate. In order to retain the valve 151 in specific position longitudinally, a retaining means 151b may be positioned on the stem 151a to bear against annular bearing 150a. The foregoing structure assures that opening 148a will be open throughout 360° travel of the valve 151 and that the valve opening 152 will be open to a varying extent for approximately 315° and closed for approximately 45°.

The reservoir and administration tube assembly, module E, comprises a cylindrical tube 161 extending from the bottom 148 of tube 139 to form a chamber 162 having a vent valve 164 in communication therewith. It should be noted that vent valve 164 is structurally like previously described vent valve 119. The lowermost position 165 of the tube 161 is tapered inwardly and is connected to flexible tubing 169 which in turn is connected to infusion site 170. The infusion site 170 includes a horizontal barrel 171 having an intermediate inlet 171a connected to tubing 169 and an opposing outlet 171b connected to flexible tubing 172. Each end of the barrel mounts a sealing diaphragm 171c which may be pierced by suitable injection equipment. Spring clamp 173 controls flow through tube 172 to yet another infusion site 174 which is structurally like infusion site 170. Cannula 180 is connected to infusion site 174 by means of flexible tube 176.

It should be noted that vent valve passage 142 in Module D is positioned high enough above the top of float valve 144 to establish a fluid level sufficient for floatation without endangering closing of the valve during infusion. When the I.V. fluid container runs out of fluid, the valve drifts down until the valve cone segment 144a seats on the rim of seat 145, thereby preventing any air from contacting filters 147. Therefore, when the apparatus is turned upside down as when attaching a fresh I.V. container, the weight of the column of fluid in the administration tubing prevents the light weight float member from becoming dislodged. When the apparatus is resuspended in the normal position, the float is restored to the floating position by refilling the chamber with fluid and removing the vacuum below the float and any pump pressure above the float. Vent valve 142 is used to evacuate air in the chamber above the float, and vent valve 164 is used to break the vacuum below the float.

The volumetric set 1B is shown in detail in FIG. 4 of the drawings and comprises the same pump and spike module A as that of the primary set 1A. The three way valve, vent valve and burette module F is attached to module A by cylindrical housing 320 affixed to collar 301. Housing 320 terminates in a horizontal cylindrical barrel 321 containing three way valve 322 on one side and vent valve 323 on the other. The three way valve 322 comprises a tubular body 322a which is closed at both ends and rotates within barrel 321. The body 322a is provided with three holes two of which, namely 322b and 322c, are diametrically opposed and so positioned as to align with outlet 318 in the bottom 319 of housing 320. The third hole 322d is spaced approximately 90° from the other two holes and in alignment therewith. The outer end of the three-way valve 322 is provided with a diaphragm seal 324 through which additional medicaments may be introduced. The barrel 321 has a drop tube 325 extending downwardly therefrom in alignment with the openings 322b, 322c and 322d in the valve body 322a. As illustrated in FIG. 4, the valve 322 is set for fluid flow through outlet 318 into drop tube 325. Referring to FIG. 5, the valve 322 has been reset so as to cut off all flow, while in FIG. 6 the valve 322 has been set to establish flow from the diaphragm end of the valve out through drop tube 325.

The other end of barrel 321 mounts a vent valve 323 comprising a cylindrical sleeve 326 closed at its inner end 326b. The sleeve 326 is provided with an opening 326c adopted to align with hole 327 in barrel 321. Burette 328 is connected to the barrel 321 so that drops fed through drop tube 325 will fall in burette chamber 329.

The burette 328 is fluidly connected to flow meter module C which is identical to the flow meter module C of the primary set 1A. Similarly flow control module D is connected to the flow meter module C and such flow control module is exactly like that in the primary set 1A. A fluid reservoir and administration tubing-module E is connected to the module D and is exactly like module E of the primary set 1A and in addition has an attenuator assembly 330. The attenuator assembly 330 comprises an insert 331 having holes 332 closed by flap type valve 333.

Figure 7:
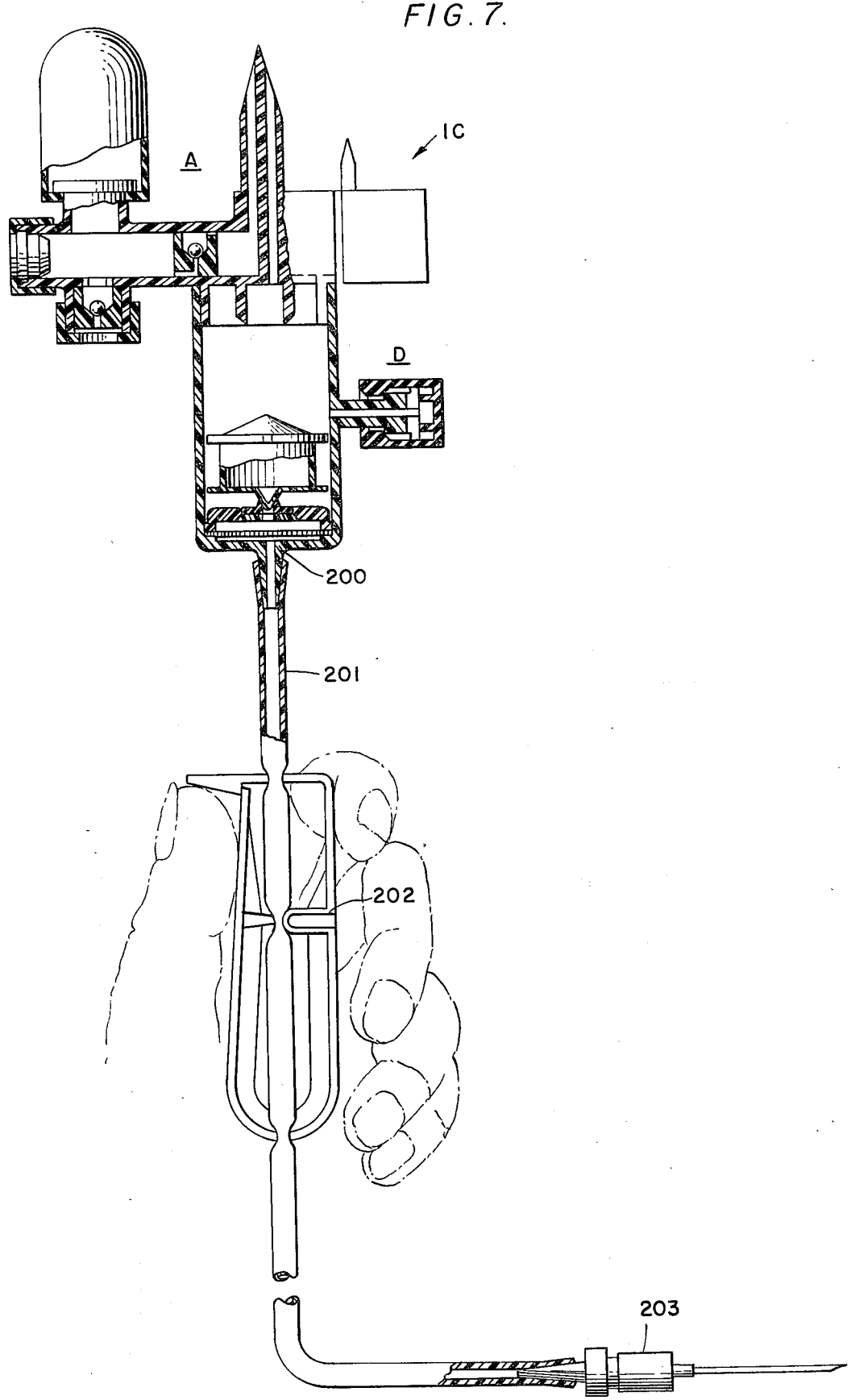
FIG. 7 is an elevational view, partly in section, of the secondary or piggyback parenteral unit.

The piggyback or secondary I.V. set 1C is shown in detail in FIG. 7 and comprises a pump and spike module A which is identical with module A of the primary set 1A. A flow control assembly module D is connected to module A and is identical to module D of the primary set 1A. Outlet 200 at the bottom of module D is connected to flexible tube 201 carrying a spring clamp 202 and a cannula assembly 203 at its end.

What I claim is:

1. An intravenous administration system having a plurality of connected intravenous units operating in a cooperative and inter-related manner to provide controlled administration of several parenteral fluids through a single cannula said system comprising:
   1. a primary intravenous set including
      a. spike means adapted to connect the set to a container of intravenous fluid, conduit means connected to said spike means for conducting fluid from the intravenous fluid container,
      b. vent means in communication with the conduit means,
      c. a flowmeter connected to the aforesaid conduit means,
      d. anti-air lock and anti-air embolism means connected to the outlet end of the flowmeter,
      e. a flow control assembly connected to the aforesaid anti-air lock and anti-air embolism means, and adaptive means positioned ahead of the flowmeter for receiving the fluid connector of a secondary IV, said means incorporating a check valve for prevention of fluid flow from a primary IV container to a secondary, and a second check valve for prevention of fluid flow from a secondary to the primary,
      f. a fluid reservoir and administration assembly in communication with the flow control assembly for administering the intravenous fluid to the patient,
   2. a volumetric intravenous set including
      a. spike means adapted to connect the set to a container of intravenous fluid, conduit means connected to said spike, means for conducting intravenous fluid from the intravenous fluid container,
      b. a valve controlling flow through the conduit means, a vent valve in communication with the conduit means, a volumetric reservoir connected to the aforesaid conduit means,
      c. a flow meter connected fluidly to the aforesaid volumetric reservoir,
      d. a flow control assembly connected to the flow meter, and
      e. a fluid reservoir and administration assembly connected at one end to the flow control assembly and at the other end to the administration assembly of the primary set, and
   3. a secondary intravenous set including
      a. spike means adapted to connect the set to a container of intravenous fluid, conduit means connected to said spike, means for conducting intravenous fluid from the intravenous fluid container,
      b. anti-air lock and anti-air embolism means connected to the aforesaid conduit means, and
      c. administration means connected to the anti-air lock and anti-air emolism means, said administration means including a cannula fluidly connected to the primary set above the flow meter whereby intravenous fluid from the secondary set is fed into the primary set for administration thereby.

2. The invention as set forth in claim 1 and wherein valve means are provided in the primary set above the flow meter to selectively and automatically control flow from the secondary set and the primary set wherein flow is first fed from the secondary set and upon cessation thereof flow from the primary set immediately commences.

3. The invention as set forth in claim 2 and wherein check valves are provided so that upon the cessation of flow from the secondary set flow immediately commences from the primary set.

4. The invention as set forth in claim 1 and wherein the flow control assembly in the primary set and the volumetric set each include means to prevent air emboli from entering the administration assembly.

5. The invention as set forth in claim 4 and wherein the means to prevent air emboli from entering the administration assembly comprises a float valve and seat combination which upon the exhaustion of flowing fluid causes the valve to come to rest on the seat to close off communication, the valve being held onto the seat by the vacuum developed beneath the seat by the downward movement of the fluid therebeneath.

6. The invention as in claim 4 wherein means are provided to prevent filter air lock and inadvertent air emboli when the IV set is inverted as when adapting the unit to a fresh I.V. container.

7. The invention in claim 6 wherein said means comprises a clamp for closing off the administration means.

8. The invention as set forth in claim 1 and wherein the flow control assembly in both the primary set and the volumetric set includes a flow control valve comprising a cylindrical barrel having an inlet in communication with the flow meter and an outlet in communication with the fluid reservoir, a cylindrical valve body rotatably carried within the barrel, said body mounting a valve which opens and closes the barrel outlet to control flow of the intravenous fluid.

9. The invention as set forth in claim 8 and wherein the valve comprises a tapered element fitting on the periphery of the valve body to vary opening of the barrel outlet in response to rotation of the valve body.

10. The invention as set forth in claim 1 and wherein in the primary set, the volumetric set, and the secondary set the spike means in each set is provided with an air inlet passage and an intravenous fluid outlet passage and further wherein each set is provided with a pump connected to the air inlet of the spike means for introducing air into the intravenous fluid reservoir to cause flow of the fluid therein.

11. The invention as set forth in claim 10 and wherein a check valve is located on the inlet and outlet side of the pump and further wherein an air filter is provided on the pump inlet side.

12. The invention as set forth in claim 1 and wherein the vent means in the primary and volumetric set includes a main check valve in the conduit means, a passage branched off from the conduit means beneath the main check valve, a secondary check valve in said passage, an infusion site on the passage outward of the secondary check valve, a second passage branched from the conduit means beneath the main check valve and a vent valve in said second passage.

13. The invention as set forth in claim 12 and wherein the flow control assembly in both the primary and volumetric sets comprises an anti-air lock chamber, a drop tube in communication with the flow meter outlet and feeding into the anti-air lock chamber, a vent valve in communication with said anti-air lock chamber, said anti-air lock chamber having an outlet in its lower portion, a float valve in the anti-air lock chamber outlet, and an adjustable flow control valve in communcation with the anti-air lock chamber outlet for controlling flow therefrom.

14. The invention as set forth in claim 13 and wherein on both the primary set and volumetric set a micro-drop tube is in fluid communication with the flow control valve, a reservoir for receiving fluid from the micro-drop tube, a vent valve connected to the aforesaid reservoir, the reservoir having an outlet at the lower extremity, a flexible tube connected to the outlet, a flexible clamp mounted on the flexible tubing to control fluid therethrough, an infusion site fluidly connected to said tubing and distal to the clamp, and a cannula assembly connected to the end of the tubing.

15. The invention as set forth in claim 14 and wherein in the primary set, the volumetric set, and the secondary set micron filtering means is provided immediately below the float valve.

16. The invention as set forth in claim 12 and wherein in both the primary set and the volumetric set, the flow meter includes a tapered tube which is smallest at its upper end, a float member fluidly carried in said tube, said float member having an indicia element thereon cooperating with scales carried on the meter tube.

17. The invention as set forth in claim 16 and wherein the flow meter tube has a base closing off the lower end of the tube, said base having means on its upper surface portion facing the float for removing air emboli from the bottom portion of said float, said means comprising a central restricting hole extending through the base and a plurality of radially extending grooves in the upper surface portion of the base connected to the central hole whereby when the float rests on the upper surface of the tube flow must occur only through the grooves and central hole providing a restricted flow thereby increasing velocity to maintain desired flow quantity, such velocity being sufficient to wash out any air emboli in the bottom of the float.

18. A primary intravenous set comprising:
a. means adapted to connect the primary set to a container of intravenous fluid, conduit means connected to the aforesaid means for conducting fluid from the intravenous fluid container,
b. vent means in communication with the conduit means,
c. a flowmeter having an inlet and an outlet with the inlet connected to the aforesaid conduit means,
d. adaptive means positioned ahead of the flowmeter for receiving the fluid connector of a secondary intravenous set, said means incorporating a check valve for prevention of fluid flow from the primary intravenous container to a secondary set, and a second check valve for prevention of fluid flow from a secondary set to the primary set,
e. anti-air lock and anti-air embolism means connected to the outlet end of the flowmeter,
f. a flow control assembly connected to the aforesaid anti-air lock and anti-air embolism means, said flow control assembly comprising a horizontal cylindrical housing having an opening in fluid communication with the anti-air lock and anti-air embolism means, said housing having an outlet diametrical from the aforesaid opening, a cylindrical valve rotatably positioned with the housing, the valve including a cylindrical body having a raised peripheral valve surface graduated to cooperate with the housing outlet to vary flow therethrough upon rotation of the valve body, and
g. a fluid reservoir and administration assembly in communication with the flow control assembly for administering the intravenous fluid to the patient.

19. The invention as set forth in claim 18 and wherein the outlet in the valve housing is pie-shaped to cooperate with the peripheral valve element on the cylindrical valve body to provide fine and accurate flow control.

20. The invention as set forth in claim 18 and wherein the anti-air lock and anti-air embolism means comprises an anti-air lock chamber, a drop tube in communication with the flowmeter outlet and fed into the anti-air lock chamber, a vent valve in communication with said anti-air lock chamber, said chamber having an outlet in its lower position, and a float valve in the anti-air lock chamber.

21. The invention as set forth in claim 20 and wherein the vent means includes a main check valve in the conduit means, a passage branched off from the conduit means beneath the main check valve, a secondary check valve in said passage, an infusion site on the passage outward of the secondary check valve, a second passage branched from the conduit means beneath the main check valve and a vent valve in said second passage.

22. The invention as set forth in claim 21 and wherein the flowmeter includes a tapered tube which is smallest at its upper end, a float member fluidly carried in said tube, said float member having an indicia element thereon cooperating with scales carried on the meter tube.

23. The invention as set forth in claim 22 and wherein the flowmeter tube has a base closing off the lower end of the tube, said base having means on its upper surface portion facing the float for removing air emboli from the bottom portion of said float, said means comprising a central restricting hole extending through the base and a plurality of radially extending grooves in the upper surface portion of the base connected to the central hole whereby when the float rests on the upper surface of the tube base flow must occur only through the grooves and central hole providing a restricted flow thereby increasing velocity to maintain desired flow quantity, such velocity being sufficient to wash out any air emboli in the bottom of the float.

* * * * *